(12) United States Patent
Lee

(10) Patent No.: US 10,357,349 B2
(45) Date of Patent: Jul. 23, 2019

(54) FILLER FOR REMOVING WRINKLES

(71) Applicant: HBMEDICALS CO., LTD., Incheon (KR)

(72) Inventor: Hoon-Bum Lee, Incheon (KR)

(73) Assignee: HBMEDICALS CO., LTD., Incheon (KR)

( * ) Notice: Subject to any disclaimer, the term of this patent is extended or adjusted under 35 U.S.C. 154(b) by 323 days.

(21) Appl. No.: 15/335,757

(22) Filed: Oct. 27, 2016

(65) Prior Publication Data
US 2017/0042653 A1 Feb. 16, 2017

Related U.S. Application Data

(63) Continuation of application No. 14/114,184, filed as application No. PCT/KR2012/003291 on Apr. 27, 2012, now abandoned.

(30) Foreign Application Priority Data

Apr. 28, 2011 (KR) .................. 10-2011-0040057

(51) Int. Cl.
*A61F 2/00* (2006.01)
*A61L 27/16* (2006.01)
(Continued)

(52) U.S. Cl.
CPC ............ *A61F 2/0059* (2013.01); *A61L 27/16* (2013.01); *A61L 27/165* (2013.01); *A61L 27/18* (2013.01);
(Continued)

(58) Field of Classification Search
CPC ........ A61F 2/0059; A61L 27/20; A61L 27/58; A61L 27/54; A61L 27/18; A61L 27/16; A61L 27/165
See application file for complete search history.

(56) References Cited

U.S. PATENT DOCUMENTS

| 4,034,763 A | 7/1977 | Frazier |
| 5,262,418 A | 11/1993 | Van Daele et al. |

(Continued)

FOREIGN PATENT DOCUMENTS

| CN | 1977779 A | 6/2007 |
| CN | 101385669 A | 3/2009 |

(Continued)

OTHER PUBLICATIONS

Chinese Office Action dated Jun. 7, 2016 with English Translation.
(Continued)

*Primary Examiner* — Richard G Louis
(74) *Attorney, Agent, or Firm* — Cantor Colburn LLP

(57) ABSTRACT

The present invention relates to a filler for removing wrinkles, which comprises: a thin and long tubular main body to be placed so as to penetrate through subcutaneous tissue; and through-holes for guiding tissue cells surrounding the main body into the main body, so as to form fibrous tissue, wherein the through-holes are formed so as to communicate with a hollow portion formed in said main body in the lengthwise direction from the outer surface of said main body. The filler for removing wrinkles according to the present invention is prevented from being deformed or moved by pressure on the skin or by an external force arising after being inserted into the subcutaneous tissue, and can be applied to various body parts having wrinkles, including deep wrinkles. Furthermore, the wrinkle-removing effects of the filler of the present invention may last (semi)permanently.

15 Claims, 7 Drawing Sheets

(51) Int. Cl.
   *A61L 27/18* (2006.01)
   *A61L 27/54* (2006.01)
   *A61L 27/58* (2006.01)
   *A61L 27/20* (2006.01)
   *A61B 17/00* (2006.01)
   *A61B 17/06* (2006.01)

(52) U.S. Cl.
   CPC ............... *A61L 27/20* (2013.01); *A61L 27/54* (2013.01); *A61L 27/58* (2013.01); *A61B 2017/00792* (2013.01); *A61B 2017/06176* (2013.01); *A61B 2017/06185* (2013.01); *A61L 2300/414* (2013.01)

(56) References Cited

U.S. PATENT DOCUMENTS

| | | | |
|---|---|---|---|
| 5,556,426 A * | 9/1996 | Popadiuk | A61F 2/06 623/1.33 |
| 5,620,418 A * | 4/1997 | O'Neill | A61M 25/0023 604/103.08 |
| 5,769,884 A | 6/1998 | Solovay | |
| 6,245,040 B1 * | 6/2001 | Inderbitzen | A61M 25/104 604/103.07 |
| 6,517,571 B1 | 2/2003 | Brauker et al. | |
| 2002/0015957 A1 | 2/2002 | Hageman et al. | |
| 2002/0090725 A1 | 7/2002 | Simpson et al. | |
| 2002/0123790 A1 | 9/2002 | White et al. | |
| 2002/0151957 A1 | 10/2002 | Kerr | |
| 2002/0198544 A1 | 12/2002 | Uflacker | |
| 2004/0034407 A1 | 2/2004 | Sherry | |
| 2004/0098095 A1 | 5/2004 | Burnside et al. | |
| 2005/0152943 A1 | 7/2005 | Hezi-Yamit et al. | |
| 2005/0283256 A1 | 12/2005 | Sommerich et al. | |
| 2006/0058735 A1 | 3/2006 | Lesh | |
| 2006/0129222 A1 | 6/2006 | Stinson | |
| 2007/0293892 A1 | 12/2007 | Takasu | |
| 2008/0125871 A1 * | 5/2008 | Fard | A61F 2/0059 623/23.72 |
| 2008/0275569 A1 | 11/2008 | Lesh | |
| 2009/0024226 A1 * | 1/2009 | Lesh | A61F 2/0059 623/23.72 |
| 2009/0099597 A1 | 4/2009 | Isse | |
| 2010/0030241 A1 | 2/2010 | Yeung et al. | |
| 2010/0057196 A1 | 3/2010 | Pathak | |
| 2010/0154197 A1 | 6/2010 | Palmaz et al. | |
| 2010/0160961 A1 | 6/2010 | Nawrocki et al. | |
| 2011/0137331 A1 * | 6/2011 | Walsh | A61F 2/013 606/194 |
| 2012/0310367 A1 | 12/2012 | Connor | |

FOREIGN PATENT DOCUMENTS

| | | |
|---|---|---|
| JP | 08038520 | 2/1996 |
| JP | 2007330593 | 12/2007 |
| KR | 100745571 | 8/2007 |
| KR | 100888082 | 3/2009 |
| KR | 1020100058650 | 6/2010 |
| KR | 1020100124597 | 11/2010 |
| WO | 2011000788 | 1/2011 |

OTHER PUBLICATIONS

Chinese Office Action—Chinese Application No. 201280031768.4 dated Feb. 14, 2016, citing enumerated references.

Chinese Office Action—CN Application No. 201280031768.4 dated Mar. 17, 2015.

European Search Report—EP Application No. EP12776120 dated Jan. 7, 2015.

International Search Report—PCT/KR2012/003291 dated Nov. 28, 2012.

* cited by examiner

【Fig. 1】
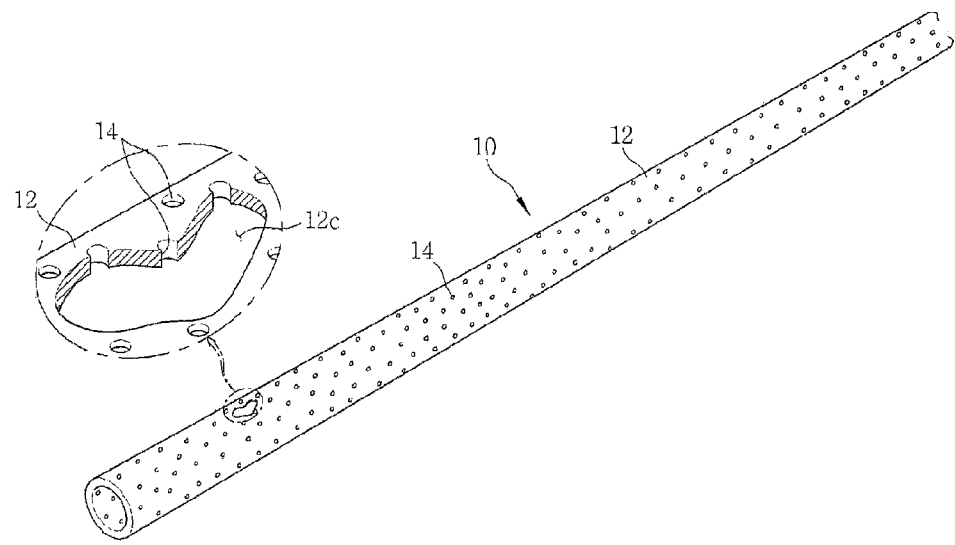
【Fig. 2】
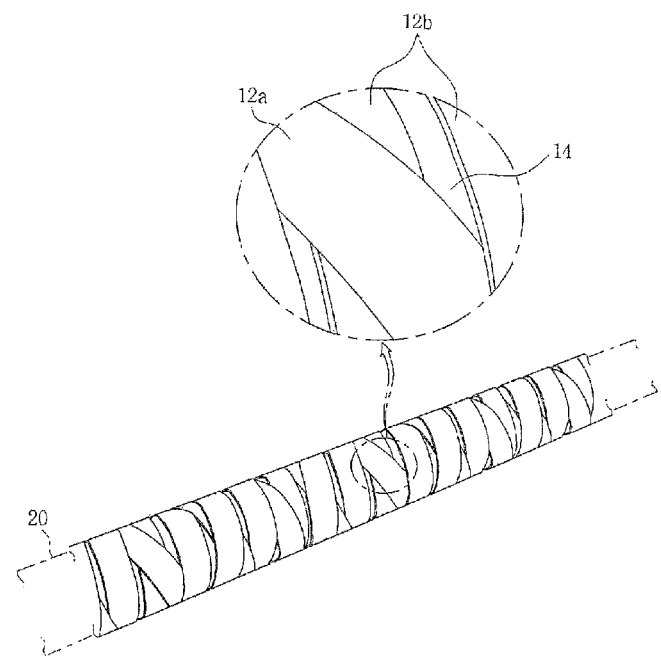

[Fig. 3]
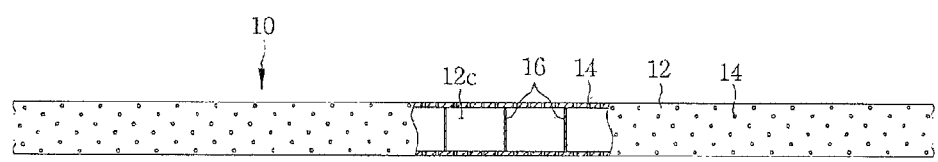
[Fig. 4]
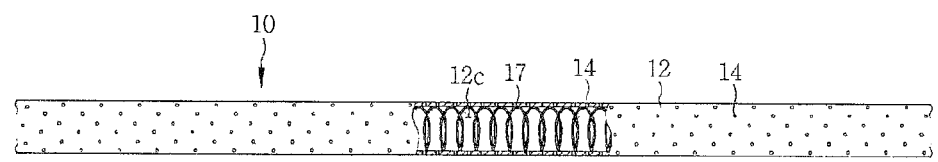

[Fig. 5]
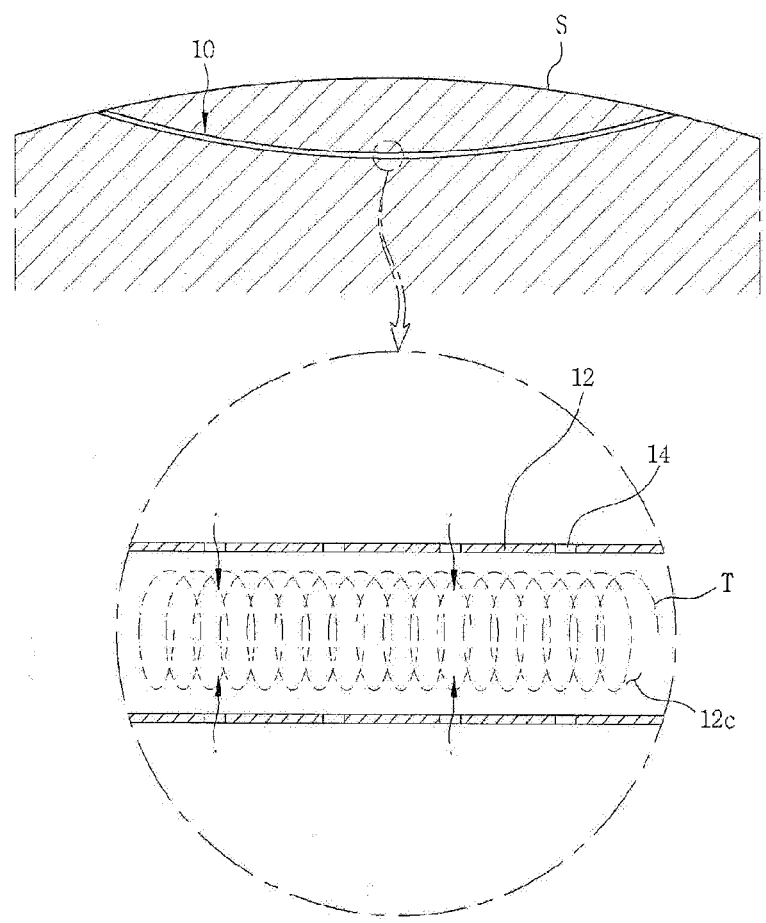
[Fig. 6]
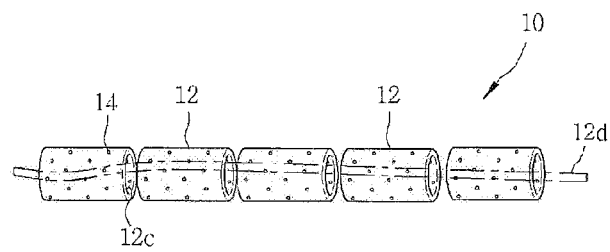

[Fig. 7]
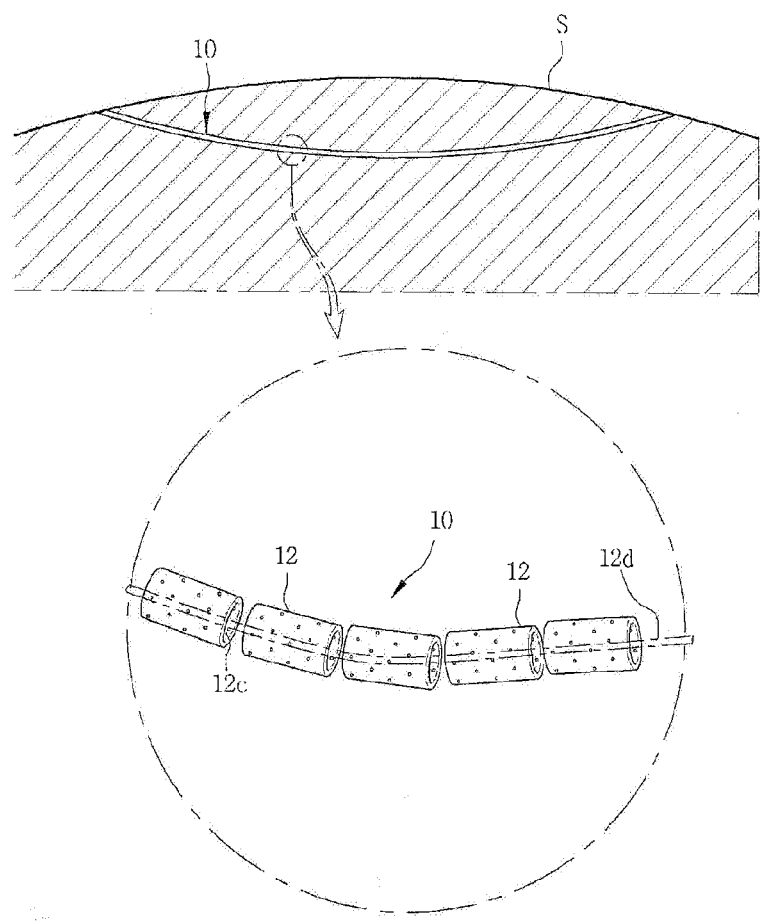

[Fig. 8]
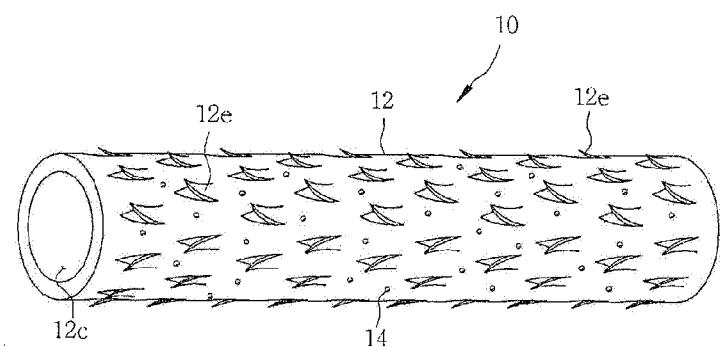

[Fig. 9]
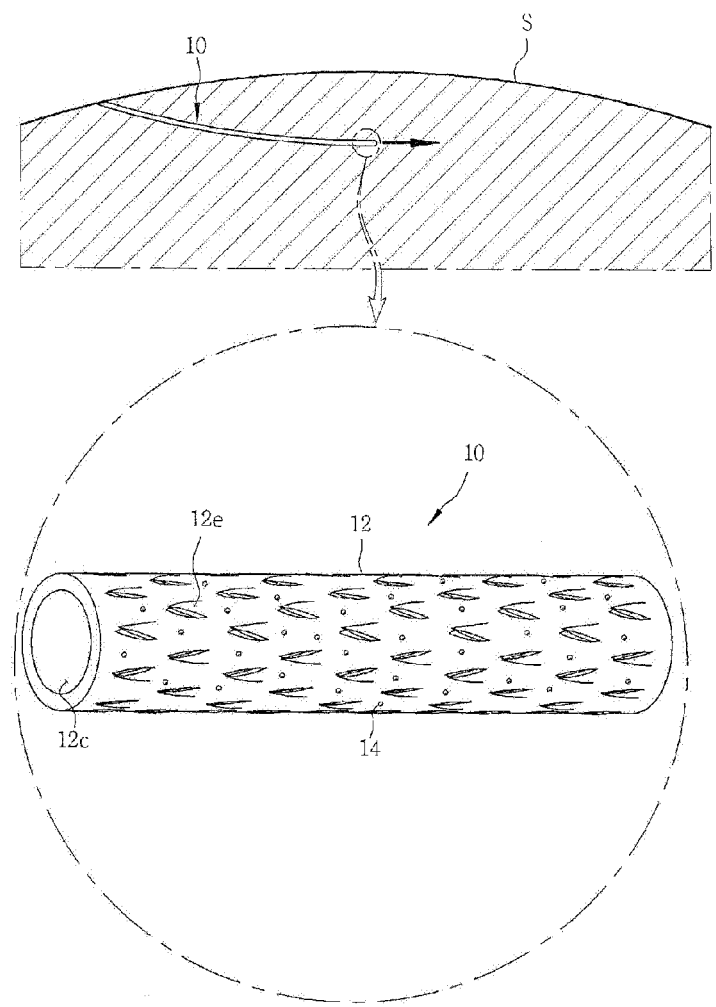

[Fig. 10]
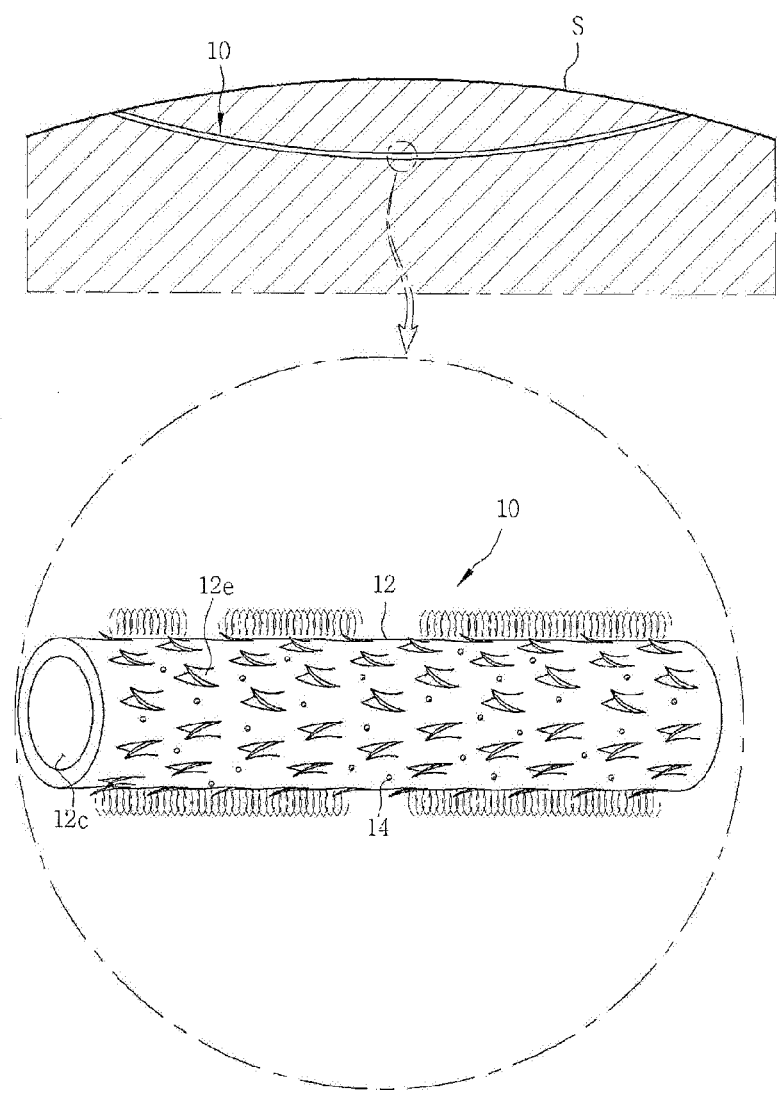

FILLER FOR REMOVING WRINKLES

CROSS REFERENCE TO RELATED APPLICATIONS

This application is a continuation of U.S. Application No. 14/114,184, filed on Oct. 25, 2013, which is a National Stage application of PCT/KR2012/003291, filed Apr. 27, 2012, which claims the benefit of Korean Patent Application No. 10-2011-0040057 filed on Apr. 28, 2011, each of which is incorporated by reference in their entirety herein.

TECHNICAL FIELD

The present disclosure relates to a filler for removing wrinkles, more particularly to a filler which is inserted into the subcutaneous layer around wrinkles through cosmetic surgery and removes the wrinkles by inducing formation of new fibrous tissue.

BACKGROUND ART

As human ages, wrinkles are formed on the skin surface of the face or body. The wrinkles are formed because of muscular contraction. The wrinkles are formed perpendicularly to the direction of muscle contraction and become deeper with aging.

As a method for removing wrinkles, Botox is frequently used to paralyze the muscles which cause wrinkles. However, this results in an unnatural look and is limited in removing the wrinkles below the eyes, below the lower lip and around the mouth and in removing thick or deep wrinkles. Also, the effect lasts only 3-6 months.

As another method, a filler is used to correct wrinkles and other depressions in the skin. Although a liquid filler is convenient to inject, it tends to move toward the direction of muscle contraction after being injected into the skin. As a result, the wrinkles may look deeper and, it is limited in that it is degraded and absorbed by the body after a predetermined time (up to about 1-2 years).

Another method is to insert a very thin gold thread into the subcutaneous layer. The gold thread induces growth of new tissue around the thread through foreign body reactions. However, this method is limited to be used for thick wrinkles and the inserted gold thread may be bent by external force or protrude out of the skin. Also, it may cause diagnostic problems during X-ray, CT or MRI imaging through interference.

DISCLOSURE

Technical Problem

The present disclosure is directed to providing a filler for removing wrinkles that is not moved after being inserted into the subcutaneous layer without resorting, for example, to surgical skin incision regardless of muscle contraction.

The present disclosure is also directed to providing a filler for removing wrinkles that provides (semi)permanently lasting wrinkle-removing effect after being inserted into the subcutaneous layer even when the filler itself is degraded and absorbed by the body with time since it induces formation of new fibrous tissue including collagen fiber.

The present disclosure is also directed to providing a filler for removing wrinkles that can be applied to various wrinkles including thick wrinkles and has recoiling force against external force.

Technical Solution

In a general aspect, there is provided a filler for removing wrinkles, including: a thin and long tubular main body provided so as to penetrate the subcutaneous layer; and through-holes provided so as to guide tissue cells surrounding the main body into the main body to form fibrous tissue, wherein the through-holes are formed to communicate with a hollow portion formed in the main body in a lengthwise direction from the outer surface of the main body.

In an exemplary embodiment of the present disclosure, the main body of the filler for removing wrinkles has a circular transection.

Specifically, the main body may have an outer diameter of 0.6-1.0 mm, the hollow portion may have a diameter (inner diameter of the main body) of 0.5-0.7 mm, and the through-holes may have a diameter of 40-500 μm.

In an exemplary embodiment of the present disclosure, the main body of the filler for removing wrinkles is made of an elastic material.

In another exemplary embodiment of the present disclosure, the main body of the filler for removing wrinkles is made of a biodegradable polymer selected from a group consisting of hyaluronic acid (HA), polylactic acid (PLA), polyglyco-lactic acid (PGLA) and polydioxanone (PDS).

In another exemplary embodiment of the present disclosure, the main body of the filler for removing wrinkles is made of a non-biodegradable polymer selected from a group consisting of nylon, silicone and Teflon.

In another exemplary embodiment of the present disclosure, the main body may have a double-layer structure including an inner sheath and an outer sheath made of different materials having different physical properties.

In another exemplary embodiment of the present disclosure, a plurality of partitions may be further formed in the hollow portion in the main body of the filler for removing wrinkles.

In another exemplary embodiment of the present disclosure, a spiral elastic support may be further formed in the hollow portion in the main body of the filler for removing wrinkles.

In another exemplary embodiment of the present disclosure, a spiral elastic support may be provided outside the main body of the filler for removing wrinkles so as to surround the outer surface of the main body.

Advantageous Effects

Since a filler for removing wrinkles according to the present disclosure has recoiling force, it is not deformed or moved by the pressure or external force applied on the skin after being inserted into the subcutaneous layer. Since a large quantity of new fibrous tissue including collagen fiber can be formed in a hollow portion of a main body of the filler through through-holes provided on the outer surface of the main body, the filler can be applied to various wrinkles including thick wrinkles by adjusting the diameter of the main body, the diameter of the hollow portion, the diameter of the through-holes, etc. depending on the size and kind of the wrinkles. Furthermore, the wrinkle-removing effect may last (semi)permanently since new fibrous tissue is formed.

DESCRIPTION OF DRAWINGS

FIG. 1 is a perspective view of a filler for removing wrinkles according to an exemplary embodiment of the present disclosure.

FIG. 2 is a perspective view of a filler for removing wrinkles according to another exemplary embodiment of the present disclosure.

FIG. 3 is a longitudinal sectional view of a filler for removing wrinkles according to another exemplary embodiment of the present disclosure wherein partitions are formed.

FIG. 4 is a longitudinal sectional view of a filler for removing wrinkles according to another exemplary embodiment of the present disclosure wherein a spiral elastic support is provided.

FIG. 5 shows fibrous tissue formed in a hollow portion of a filler for removing wrinkles according to the present disclosure inserted into the subcutaneous layer.

FIG. 6 shows a filler for removing wrinkles according to another exemplary embodiment of the present disclosure which is improved to allow easy insertion into a curved part.

FIG. 7 shows the filler for removing wrinkles according to the embodiment shown in FIG. 6 which is inserted into a curved part.

FIG. 8 shows a filler for removing wrinkles according to another exemplary embodiment of the present disclosure wherein elastic cogs projecting in one direction are provided on the outer surface of a main body of the filler for removing wrinkles.

FIG. 9 shows the filler for removing wrinkles according to the embodiment shown in FIG. 8 being inserted into the subcutaneous layer.

FIG. 10 shows the filler for removing wrinkles according to the embodiment shown in FIG. 8 inserted into the subcutaneous layer.

MODE FOR INVENTION

Hereinafter, the embodiments of the present disclosure will be described in detail referring to the attached drawings.

FIG. 1 is a perspective view of a filler for removing wrinkles according to an exemplary embodiment (first embodiment) of the present disclosure. As shown in FIG. 1, a filler 10 for removing wrinkles according to the present disclosure includes: a thin and long, integral tubular main body 12 provided so as to penetrate the subcutaneous layer; and through-holes 14 provided so as to guide tissue cells surrounding the main body 12 into the main body 12 to form fibrous tissue, wherein the through-holes 14 are formed to communicate with a hollow portion 12c formed in the main body 12 in a lengthwise direction from the outer surface of the main body 12.

In another exemplary embodiment (second embodiment) of the present disclosure shown in FIG. 2, the filler 10 for removing wrinkles may have, for example, a circular transection (Also, it may have a hexagonal transection.). The thin and long tubular main body 12 may be formed by spirally winding a plurality of strip-shaped parts 12a, 12b which is made of the material of the main body 12 of the filler 10 for removing wrinkles and which is having a predetermined width b along the surface of a long core material 20 having a diameter desired for the hollow portion 12c so as to cross each other (in a manner similar to making a bamboo wife from bamboo cane). Then, the core material 20 may be removed, such that the hollow portion 12c is formed in the parts 12a, 12b in a lengthwise direction, and the through-holes 14 may be formed by the gaps between the parts 12a, 12b (including the gaps formed at the crossing of the parts). Alternatively, the thin and long tubular main body 12 may be formed by various methods which are spirally winding the plurality of parts 12a, 12b so as to cross each other, without using the core material. Although FIG. 2 shows an example wherein two parts 12a, 12b, i.e. a first part 12a and a second part 12b, are used to form the filler 10 for removing wrinkles according to the present disclosure, it will be obvious to those skilled in the art that the thin and long tubular main body 12 may be formed by spirally winding a plurality of strip-shaped parts as to cross each other, without being limited thereto.

In the exemplary embodiments of the present disclosure including the first embodiment and the second embodiment described above, the main body 12 may have a circular or polygonal (e.g., tetragonal, hexagonal, octagonal, etc.) transection. Specifically, it may have a circular transection, so that it can be easily inserted into the subcutaneous layer after being threaded on a needle (e.g., a needle for cosmetic surgery). Specifically, the main body 12 may have a diameter of 0.6-1.0 mm, so that it can be easily inserted into the subcutaneous layer and be located between the subcutaneous fat layer and the dermis or in the fat layer after being inserted. The length of the main body 12 is not particularly limited as long as it is enough for insertion.

The hollow portion 12c formed in the main body 12 in the lengthwise direction provides a space, so that nearby tissue cells such as fibroblasts are guided through the through-holes 14 and then fibrous tissue such as elastic fibrous tissue and collagen tissue is newly formed. Accordingly, since the amount of newly formed fibrous tissue increases as the diameter of the hollow portion 12c is larger and the amount of newly formed fibrous tissue decreases as the diameter of the hollow portion 12c is smaller, the diameter of the hollow portion 12c may be adequately adjusted depending on the depth, location, etc. of wrinkles. In general, the diameter of the hollow portion 12c may be 0.5-0.7 mm.

The through-holes 14 provide a passage for fibroblasts, etc. to enter the hollow portion 12c. They may have any shape, including circular, triangular, tetragonal, octagonal, trapezoidal and rhombic shapes. The plurality of through-holes 14 may be arranged regularly or irregularly on the outer surface of the main body 12. Specifically, the through-holes 14 may have a diameter, when they have a circular shape, or a circle-equivalent diameter, when they have other shapes, of 40-500 μm. If the diameter is too large, the filler 10 may not be able to support the surrounding tissues.

Specifically, the main body 12 may be made of an elastic material. It may be made of a biodegradable polymer such as hyaluronic acid (HA), polylactic acid (PLA), polyglycolactic acid (PGLA) and polydioxanone (PDS) or a non-biodegradable polymer such as nylon, silicone and Teflon. If a biodegradable polymer is used, the filler for removing wrinkles is slowly degraded and absorbed after the fibrous tissue is formed. If a non-biodegradable polymer is used, the filler for removing wrinkles remains permanently in the subcutaneous layer.

The main body 12 may have a double-layer structure including an inner sheath and an outer sheath made of different materials having different physical properties. For example, the inner sheath may be formed of a hard material and the outer sheath may be formed of a soft material. Alternatively, the inner sheath may be formed of an absorbent material and the outer sheath may be formed of a non-absorbent material, or the inner sheath and the outer sheath may be formed of absorbent materials having different rate of absorption.

The filler for removing wrinkles according to the present disclosure has recoiling force so as to endure the pressure or external force applied on the skin without collapsing after being inserted into the subcutaneous layer. In another exemplary embodiment, a plurality of partitions 16 may be formed in the hollow portion 12c to reinforce the recoiling force, as shown in FIG. 3.

The partitions 16 may be formed to completely or incompletely divide the hollow portion 12c of the main body 12. The partitions 16 may be made of the same material as the main body 12.

In another exemplary embodiment, a spiral elastic support 17 may be formed in the hollow portion 12c to reinforce the recoiling force, as shown in FIG. 4. In another exemplary embodiment, the spiral elastic support 17 may be formed outside the main body 12 so as to surround the outer surface of the main body 12. The spiral elastic support 17 may be made of the same material as the main body 12. In addition to reinforcing the recoiling force, the spiral elastic support 17 may allow easier insertion into a curved part since, when the filler for removing wrinkles according to the present disclosure is inserted into the subcutaneous layer with a curved shape, the spiral structure can become narrower or wider depending on the curvature.

In another exemplary embodiment of the present disclosure, a filler 10 for removing wrinkles as shown in FIG. 6 may be provided. In the filler 10 for removing wrinkles, a plurality of main bodies 12 are disposed in a row such that individual hollow portions 12c are adjacent to each other, and a connector 12d penetrating the hollow portions 12c formed in the main bodies 12 in a lengthwise direction is further provided so that the plurality of main bodies 12 are used as a series of fillers for removing wrinkles. According to this embodiment, the filler 10 for removing wrinkles can be more easily inserted into the subcutaneous layer with a curved shape, as shown in FIG. 7.

In another exemplary embodiment of the present disclosure, a filler 10 for removing wrinkles wherein elastic cogs 12e are formed on the outer surface of a main body 12 by partially cutting the surface may be provided, as shown in FIG. 8. In the filler 10 for removing wrinkles, the plurality of elastic cogs 12e projecting in one direction are further formed on the outer surface of the main body 12 along the lengthwise direction of the main body 12. According to this embodiment, the elastic cogs 12e remain folded (the elastic cogs are accommodated in grooves partially cut on the outer surface) in the subcutaneous layer while the filler 10 for removing wrinkles is being inserted into the subcutaneous layer, as shown in FIG. 9. Then, after the insertion of the filler 10 for removing wrinkles into the subcutaneous layer is completed, the elastic cogs 12e restore to the original state of projecting in one direction from the main body 12 (see FIG. 8) owing to elasticity, as shown in FIG. 10. The restored elastic cogs 12e are caught by tissues and prevent the filler 10 for removing wrinkles from retreating in the subcutaneous layer, thereby ensuring fixation to the subcutaneous layer.

In the filler 10 for removing wrinkles according to the present disclosure, growth factors for facilitating the formation of fibrous tissue may be coated on the outer surface or inner surface of the main body 12 or included in the main body 12. The growth factor may be angiogenesis factor, platelet-derived growth factor (PDGF), fibroblast growth factor (FGF), transforming growth factor-α (TGF-α), transforming growth factor-β (TGF-β), epidermal growth factor (EGF), connective tissue growth factor (CTGF), vascular endothelial growth factor (VEGF), etc., but is not limited thereto.

The filler for removing wrinkles according to the present disclosure may be easily inserted by threading one end thereof on a needle for cosmetic surgery or by connecting to the tip of the needle according to a commonly employed method. Hereinafter, a method for removing wrinkles using the filler for removing wrinkles according to the present disclosure will be described in detail referring to FIG. 5.

A wrinkled area to which the filler is to be inserted is marked and an anesthetic ointment is applied thereon. Then, a needle is inserted from one end of the marked area into the subcutaneous layer, particularly between the subcutaneous fat layer and the dermis or into the fat layer, and pulled at the other end, such that the filler for removing wrinkles spans over the marked area. Then, the portion coming out of the skin S is removed by cutting. Subsequently, blood, red blood cells, white blood cells, platelets, fibroblasts, myofibroblasts, etc. are filled in a hollow portion 12c of the filler 10 for removing wrinkles inserted into the subcutaneous layer.

The amount of the fibroblasts reaches maximum 3-5 days after the insertion, and that of the myofibroblasts reaches maximum at 5-15 days. Thereafter, collagen is synthesized by the fibroblasts, resulting in fibrous tissue T. The fibrous tissue T provides a wrinkle-correcting effect.

While the exemplary embodiments have been shown and described, it will be understood by those skilled in the art that various changes in form and details may be made thereto without departing from the spirit and scope of this disclosure as defined by the appended claims.

The invention claimed is:

1. A method of removing skin wrinkles, the method comprising:
   inserting a filler for removing a skin wrinkle into a subcutaneous layer of a subject in need of removing a skin wrinkle,
      wherein the filler comprises at least one thin and long tubular main body provided so as to be into the subcutaneous layer,
      wherein the main body comprises a hollow portion formed in the main body in a lengthwise direction and through-holes penetrating the main body in the direction perpendicular to the lengthwise direction to communicate with the hollow portion,
      wherein the through-holes are provided so as to guide tissue cells surrounding the main body into the hollow portion to form fibrous tissue,
      wherein the filler has recoiling force so as to endure a pressure or external force applied on a skin without collapsing after being inserted into a subcutaneous layer,
      wherein the main body is formed by spirally winding a plurality of strip-shaped parts so as to cross each other, such that the hollow portion is provided in the parts in a lengthwise direction, and the through-holes communicating with the hollow portion from the outer surface of the main body are provided by the gaps between the parts, and
      wherein the main body has a double-layer structure comprising an inner sheath and an outer sheath made of different materials having different physical properties; and
   maintaining the filler in the subcutaneous layer for days so as to fill the cells guided through the through-holes in the hollow portion, and form a fibrous tissues in the hollow portion.

2. The method according to claim 1, wherein the days are 5-15 days in order that an amount of myofibroblasts in the hollow portion reaches maximum.

3. The method according to claim 1, wherein the days are 3-5 days in order that an amount of fibroblasts in the hollow portion reaches maximum.

4. The method according to claim 1, wherein the main body is formed integrally and has a circular transection.

5. The method according to claim 1, wherein the main body has a diameter of 0.6-1.0 mm, and the hollow portion has a diameter of 0.5-0.7 mm.

6. The method according to claim 1, wherein the through-holes have a diameter or a circle-equivalent diameter of 40-500 μm.

7. The method according to claim 1, wherein the main body is made of an elastic material.

8. The method according to claim 1, wherein the main body is made of a biodegradable polymer selected from a group consisting of hyaluronic acid (HA), polylactic acid (PLA), polyglyco-lactic acid (PGLA) and polydioxanone (PDS).

9. The method according to claim 1, wherein the main body is made of a non-biodegradable polymer selected from a group consisting of nylon, silicone and Teflon.

10. The method according to claim 1, wherein a plurality of partitions are further formed in the hollow portion.

11. The method according to claim 1, wherein a spiral elastic support is further formed in the hollow portion.

12. The method according to claim 1, wherein a spiral elastic support is further provided outside the main body so as to surround the outer surface of the main body.

13. The method according to claim 1, wherein the filler comprises a second thin and long tubular main body forming a plurality of the main bodies that are disposed in a row such that the hollow portions are adjacent to each other, and a connector penetrating the hollow portions formed in the main bodies in a lengthwise direction is further provided so that the plurality of main bodies are used as a series of fillers for removing wrinkles.

14. The method according to claim 1, wherein a plurality of elastic projections projecting in one direction are further formed on the outer surface of the main body along the lengthwise direction of the main body.

15. The method according to claim 1, wherein growth factors for facilitating the formation of fibrous tissue are coated on the outer surface or inner surface of the main body or included in the main body.

* * * * *